United States Patent [19]

Murphy

[11] Patent Number: 5,665,057
[45] Date of Patent: Sep. 9, 1997

[54] HEATED BACK SUPPORTING DEVICE

[76] Inventor: Michael G. Murphy, 117 CR 110, Jonesboro, Ark. 72401

[21] Appl. No.: 618,743

[22] Filed: Mar. 20, 1996

[51] Int. Cl.⁶ .................................................. A61F 5/00
[52] U.S. Cl. .................... 602/19; 2/44; 2/311; 2/319; 607/108
[58] Field of Search .......................... 2/44, 311–312, 2/318–322; 607/108; 224/904; 602/14, 19; 606/237; D24/171; D2/627

[56] References Cited

U.S. PATENT DOCUMENTS

| Re. 35,113 | 12/1995 | Grim | 602/14 |
|---|---|---|---|
| 3,487,474 | 1/1970 | Meo | 2/311 |
| 4,790,461 | 12/1988 | Stover | 224/904 |
| 5,062,414 | 11/1991 | Grim | 128/DIG. 20 X |
| 5,122,111 | 6/1992 | Sebastian et al. | 602/19 |
| 5,259,831 | 11/1993 | LeBron | 602/19 X |
| 5,349,706 | 9/1994 | Keer | 2/44 X |
| 5,497,923 | 3/1996 | Pearson | 224/904 X |

*Primary Examiner*—Richard J. Apley
*Assistant Examiner*—David R. Risley

[57] ABSTRACT

A heated back supporting device including a belt portion having a pair of pockets formed in an interior surface thereof. The belt portion is securable around a waist of a user. A pair of heated gel packets are adapted for removable coupling within the pair of pockets formed in the interior surface of the belt portion. A plurality of utility pockets are securable to an exterior surface of the belt portion.

1 Claim, 3 Drawing Sheets

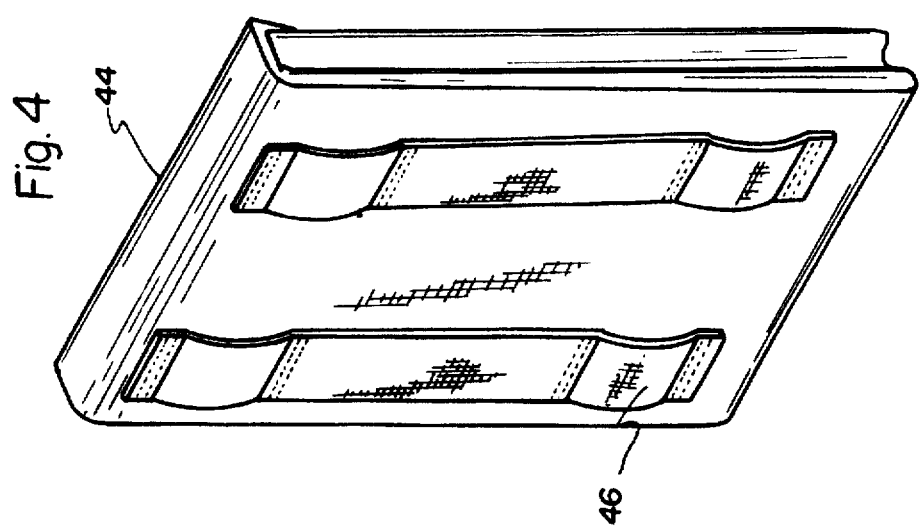
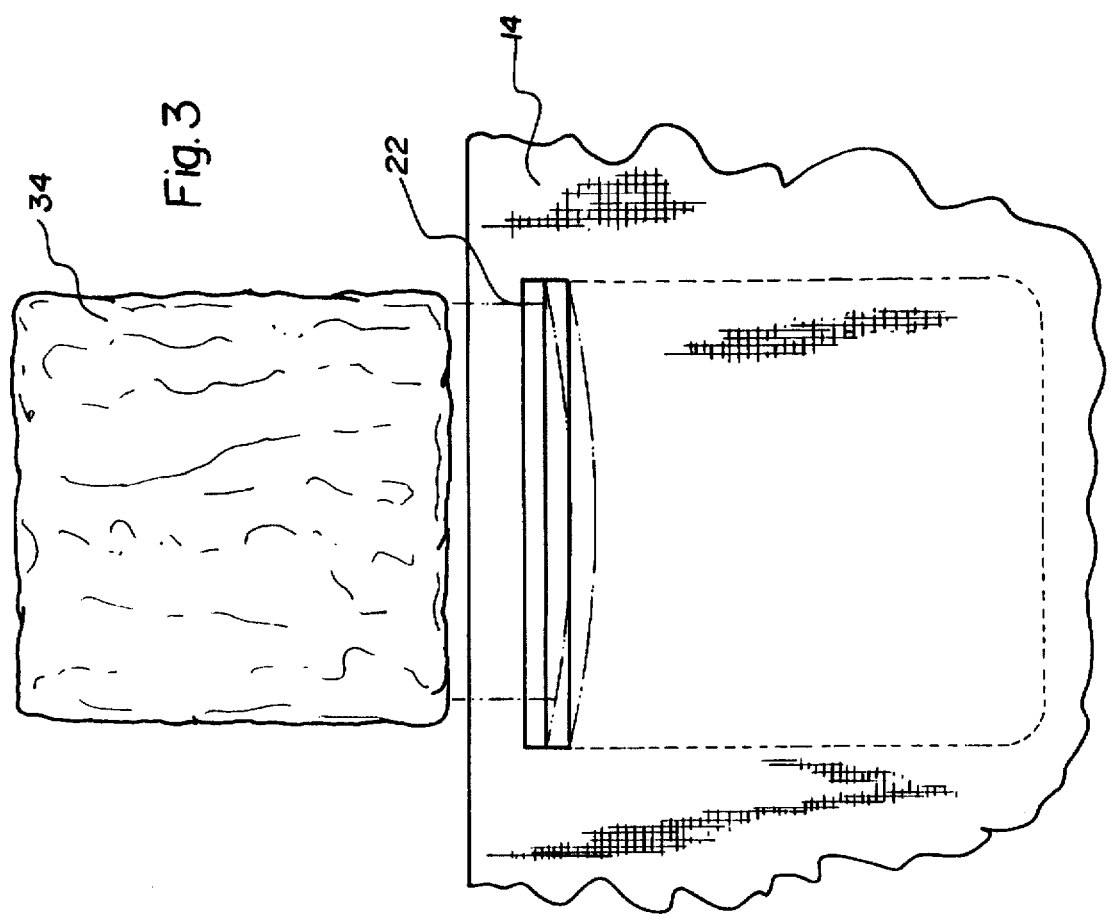

HEATED BACK SUPPORTING DEVICE

BACKGROUND OF THE INVENTION

1. Field of the Invention

The present invention relates to a heated back supporting device and more particularly pertains to allowing a user to tailor an amount of heat radiated to a preselected body portion with a heated back supporting device.

2. Description of the Prior Art

The use of heated belts is known in the prior art. More specifically, heated belts heretofore devised and utilized for the purpose of providing heat to a wearer's back are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,151,578 to Phillips discloses an anisotropically bendable heating pad.

U.S. Pat. No. 5,179,942 to Drulias et al. discloses a lumbar support therapeutic heat/cooling/air pillow belt.

U.S. Pat. No. Design 333,350 to Redira, Jr. discloses the ornamental design for a therapeutic heat transfer wrap.

U.S. Pat. No. 4,628,188 to Andreasson discloses an electric heating pad for seats and back-rests.

U.S. Pat. No. Design 274,097 to Nakao et al. discloses the ornamental design for a heat therapeutic belt.

U.S. Pat. No. Design 274,556 to Muller et al. discloses the ornamental design for a massaging and heating belt.

While these devices fulfill their respective, particular objective and requirements, the aforementioned patents do not describe a heated back supporting device for allowing a user to tailor an amount of heat radiated to a preselected body portion.

In this respect, the heated back supporting device according to the present invention substantially departs from the conventional concepts and designs of the prior art, and in doing so provides an apparatus primarily developed for the purpose of allowing a user to tailor an amount of heat radiated to a preselected body portion.

Therefore, it can be appreciated that there exists a continuing need for new and improved heated back supporting device which can be used for allowing a user to tailor an amount of heat radiated to a preselected body portion. In this regard, the present invention substantially fulfills this need.

SUMMARY OF THE INVENTION

In the view of the foregoing disadvantages inherent in the known types of heated belts now present in the prior art, the present invention provides an improved heated back supporting device. As such, the general purpose of the present invention, which will be described subsequently in greater detail, is to provide a new and improved heated back supporting device and method which has all the advantages of the prior art and none of the disadvantages.

To attain this, the present invention essentially comprises a belt portion having a generally elongated configuration. The belt portion has an interior surface and an exterior surface. The belt portion has two opposed long linear side edges and two opposed arcuate end portions. The interior surface has a pair of pockets formed therein. The exterior surface has a strap extending from one of the arcuate end portions. The strap has a pair of pile fasteners disposed thereon. The exterior surface has a dual D-ring secured to the arcuate end portion opposed from the strap. The dual D-ring couples with the strap for securement around a waist of a user. The exterior surface has a plurality of male snaps extending along the two opposed long linear side edges. A pair of heated gel packets are adapted for removable coupling within the pair of pockets formed in the interior surface of the belt portion. The device includes a pair of securement strips each having a plurality of female snaps disposed on an interior surface thereof corresponding with the plurality of male snaps extending along the two opposed long linear side edges of the belt portion for securement thereto. The device includes a plurality of utility pockets each having a pair of securement loops secured to a rear surface thereof. The securement loops are dimensioned to theadably receive the pair of securement straps therethrough for securement to the belt portion. The device includes a hammer holding portion comprised of a planar member having a pair of slots formed therethrough. The slots are dimensioned to threadably receive one of the pair of securement,straps therethrough for securement to the belt portion. The planar member has a generally U-shaped member secured to a lower portion thereof for coupling a hammer thereto.

There has thus-been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved heated back supporting device which has all the advantages of the prior art heated belts and none of the disadvantages.

It is another object of the present invention to provide a new and improved heated back supporting device which may be easily and efficiently manufactured and marketed.

It is a further object of the present invention to provide a new and improved heated back supporting device which is of durable and reliable construction.

An even further object of the present invention is to provide a new and improved heated back supporting device which is susceptible of a low cost of manufacture with regard to both materials and labor, and which accordingly is then susceptible of low prices of sale to the consuming public, thereby making such a heated back supporting device economically available to the buying public.

Still yet another object of the present invention is to provide a new and improved heated back supporting device which provides in the apparatuses and methods of the prior art some of the advantages thereof, while simultaneously overcoming some of the disadvantages normally associated therewith.

Even still another object of the present invention is to provide a new and improved heated back supporting device for allowing a user to tailor an amount of heat radiated to a preselected body portion.

Lastly, it is an object of the present invention to provide a new and improved heated back supporting device including a belt portion having a pair of pockets formed in an interior surface thereof. The belt portion is securable around a waist of a user. A pair of heated gel packets are adapted for removable coupling within the pair of pockets formed in the interior surface of the belt portion. A plurality of utility pockets are securable to an exterior surface of the belt portion.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a fragmentary view of the interior surface of the belt portion illustrating the pockets and heated gel packs.

FIG. 4 is a rear perspective view of one of the utility pockets of the present invention.

The same reference numerals refer to the same parts through the various Figures.

DESCRIPTION OF THE PREFERRED EMBODIMENT

Figure 1:
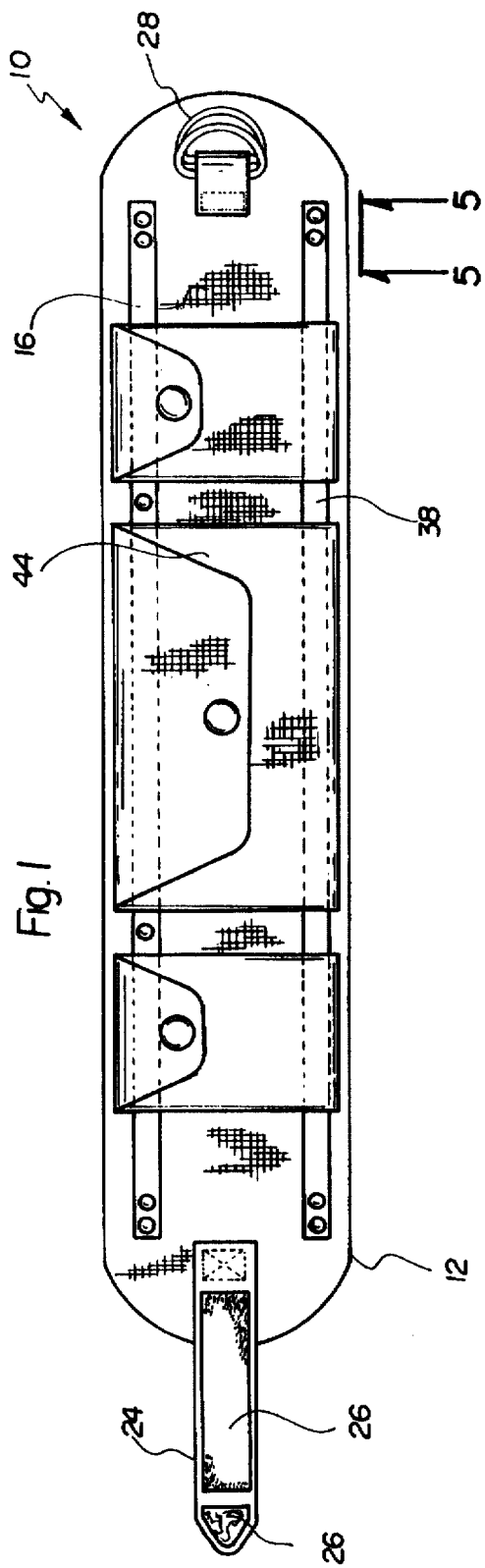
FIG. 1 is a plan view of the preferred embodiment of the heated back supporting device constructed in accordance with the principles of the present invention.
Figure 2:
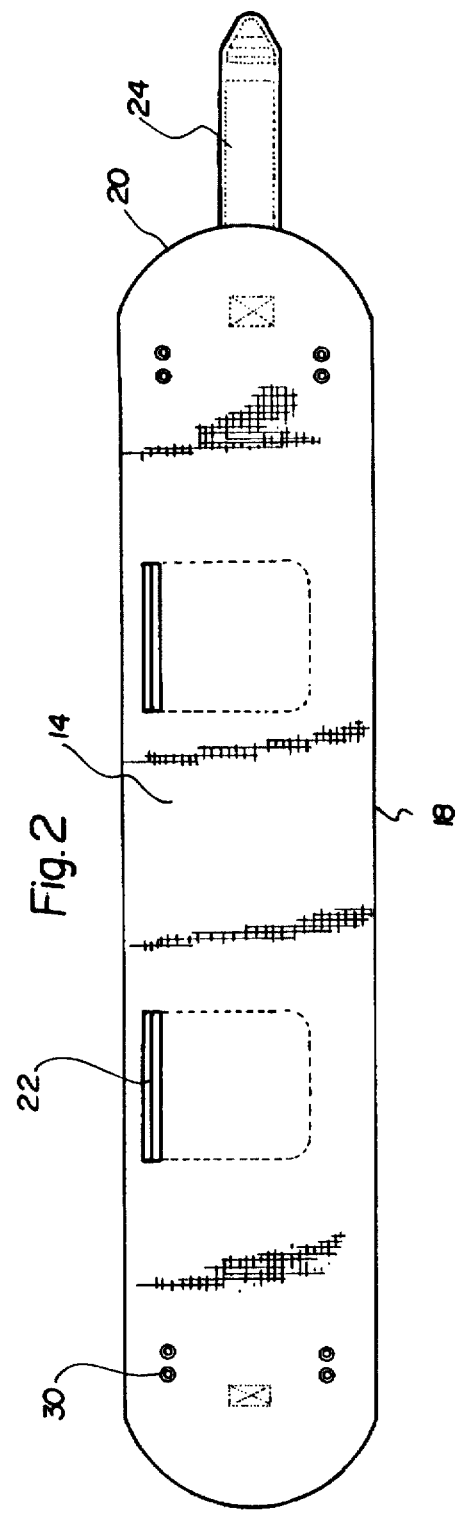
FIG. 2 is a rear elevation view of the present invention.
Figure 5:
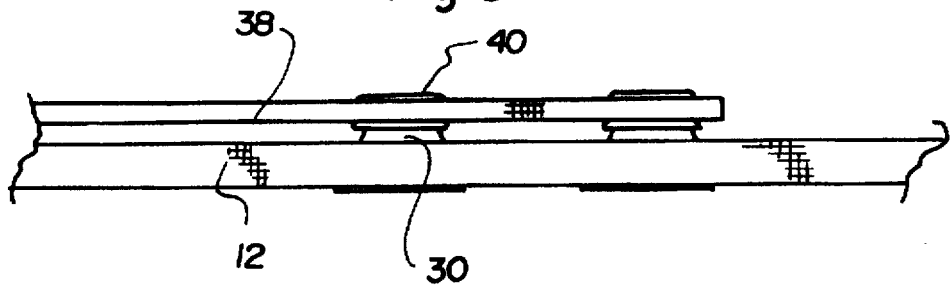
FIG. 5 is a cross-sectional view as taken along line 5—5 of FIG. 1.
Figure 6:
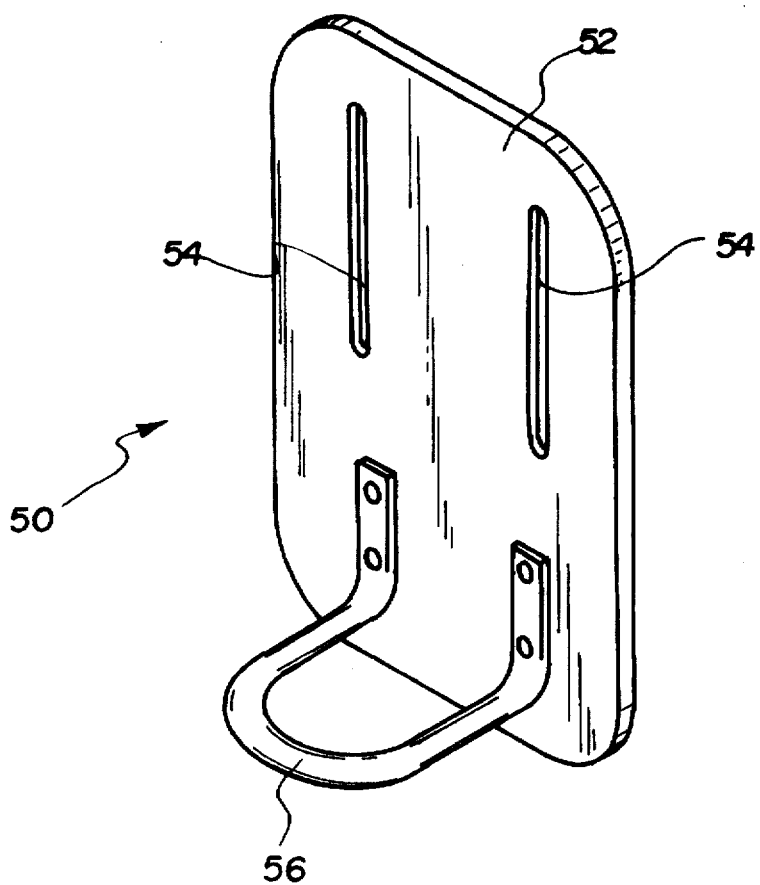
FIG. 6 is a perspective view of a hammer holding portion of the present invention.

With reference now to the drawings, and in particular, to FIG. 1–6 thereof, the preferred embodiment of the new and improved heated back supporting device embodying the principles and concepts of the present invention and generally designated by the reference number 10 will be described.

Specifically, it will be noted in the various Figures that the device relates to a new and improved heated back supporting device for allowing a user to tailor an amount of heat radiated to a preselected body portion. In its broadest context, the device consists of a belt portion, a pair of heated gel packs, a pair of securement straps, a plurality of utility pockets, and a hammer holding portion. Such components are individually configured and correlated with respect to each other so as to attain the desired objective.

The device 10 includes a belt portion 12 having a generally elongated configuration. The belt portion 12 has an interior surface 14 and an exterior surface 16. The belt portion 12 resembles other commonly available back supporters, using spandex or neoprene in its construction to create firm support. The belt portion 12 has two opposed long linear side edges 18 and two opposed arcuate end portions 20. The length of the linear side edges 18 and the width of the arcuate end portions 20 can be varied to accommodate different sized users. The interior surface 14 has a pair of pockets 22 formed therein. The pair of pockets 22 are positioned to lie over the wearer's kidney areas. The exterior surface 16 has a strap 24 extending from one of the arcuate end portions 20. The strap 24 has a pair of pile fasteners 26 disposed thereon. The exterior surface 16 has a dual D-ring 28 secured to the arcuate end portion 20 opposed from the strap 24. The dual D-ring 28 couples with the strap 24 for securement around a waist of a user. The user simply positions the belt portion 12 around their waist area and then threads the strap 24 through one of the rings of the dual D-ring 28. The user then folds the strap 24 over and threads it through the other ring of the dual D-ring 28. The pair of pile fasteners 26 are then coupled together to further secure the belt portion 12 in place. The exterior surface 16 has a plurality of male snaps 30 extending along the two opposed long linear side edges 18. An upper linear side edge has two male snaps 30 positioned at each end portion thereof and two male snaps 30 positioned therebetween. A lower linear side edge has two male snaps 30 positioned at each end portion thereof.

A pair of heated gel packets 34 are adapted for removable coupling within the pair of pockets 22 formed in the interior surface 14 of the belt portion 12. The heated gel packets 34 are standard chemical-packet style hand warmers.

The device 10 also includes a pair of securement strips 38 each having a plurality of female snaps 40 disposed on an interior surface thereof corresponding with the plurality of male snaps 30 extending along the two opposed long linear side edges 18 of the belt portion 12 for securement thereto.

Next, the device 10 includes a plurality of utility pockets 44 each having a pair of securement loops 46 secured to a rear surface thereof. The securement loops 46 are dimensioned to theadably receive the pair of securement Straps 38 therethrough for securement to the belt portion 12. The preferred number of utility pockets 44 for the device is three, one large pocket and two smaller pockets. The securement straps 38 are positioned through the securement loops 38 and are then snapped into place on the belt portion 12. Each of the utility pockets 44 has a pouch type opening including a closable flap thereover to contain tools therein. The utility pockets 44 can slide along the securement straps 38 to allow the user to easily reach them or push them out of the way. The belt portion 12 could also be used to carry sheaths for hammers, knives or other tools simply by threading one of the securement straps 38 through an opening in the sheath.

Lastly, the device 10 includes a hammer holding portion 50 comprised of a planar member 52 having a pair of slots 54 formed therethrough. The slots 54 are dimensioned to threadably receive one of the pair of securement straps 38 therethrough for securement to the belt portion 12. The planar member 52 has a generally U-shaped member 56 secured to a lower portion thereof for coupling a hammer thereto.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A heated back-supporting device for allowing a user to tailor an amount of heat radiated to a preselected body portion comprising, in combination:

a belt portion having a generally elongated configuration, the belt portion having an interior surface and an exterior surface, the belt portion having two opposed long linear side edges and two opposed arcuate end portions, the interior surface having a pair of pockets formed therein, the exterior surface having a strap extending from one of the arcuate end portions, the strap having a pair of pile fasteners disposed thereon, the exterior surface having a dual D-ring secured to the arcuate end portion opposed from the strap, the dual D-ring coupling with the strap for securement around a waist of a user, the exterior surface having a plurality of male snaps extending along the two opposed long linear side edges;

a pair of heated gel packets adapted for removable coupling within the pair of pockets formed in the interior surface of the belt portion;

a pair of securement strips each having a plurality of female snaps disposed on an interior surface thereof corresponding with the plurality of male snaps extending along the two opposed long linear side edges of the belt portion for securement thereto;

a plurality of utility pockets each having a pair of securement loops secured to a rear surface thereof, the securement loops dimensioned to theadably receive the pair of securement straps therethrough for securement to the belt portion;

a hammer holding portion comprised of a planar member having a pair of slots formed therethrough, the slots dimensioned to threadably receive one of the pair of securement straps therethrough for securement to the belt portion, the planar member having a generally U-shaped member secured to a lower portion thereof for coupling a hammer thereto.

* * * * *